United States Patent
Kowalczyk et al.

(10) Patent No.: US 11,324,601 B2
(45) Date of Patent: May 10, 2022

(54) TALUS IMPLANT

(71) Applicant: PARAGON ADVANCED TECHNOLOGIES, INC., Englewood, CO (US)

(72) Inventors: Gregory J. Kowalczyk, Little Silver, NJ (US); Selene G. Parekh, Cary, NC (US); Luciano Bernardino Bertolotti, Buenos Aires (AR)

(73) Assignee: PARAGON ADVANCED TECHNOLOGIES, INC., Englewood, CO (US)

( * ) Notice: Subject to any disclaimer, the term of this patent is extended or adjusted under 35 U.S.C. 154(b) by 0 days.

(21) Appl. No.: 16/672,505

(22) Filed: Nov. 3, 2019

(65) Prior Publication Data
US 2021/0093461 A1    Apr. 1, 2021

Related U.S. Application Data

(60) Provisional application No. 62/908,438, filed on Sep. 30, 2019.

(51) Int. Cl.
*A61F 2/42* (2006.01)
*B33Y 10/00* (2015.01)
(Continued)

(52) U.S. Cl.
CPC ........ *A61F 2/4202* (2013.01); *A61F 2/30942* (2013.01); *B29C 64/386* (2017.08);
(Continued)

(58) Field of Classification Search
CPC .. A61F 2/4202; A61F 2/32; A61F 2/36; A61F 2/3601; A61F 2/38; A61F 2/3859;
(Continued)

(56) References Cited

U.S. PATENT DOCUMENTS 3,839,742 A * 10/1974 Link ..................... A61F 2/4202
                                                    623/21.18
7,736,381 B2 *  6/2010 Biedermann ...... A61B 17/7241
                                                    606/301

(Continued)

OTHER PUBLICATIONS

Fang, Xiang, et al. "Total Talar Replacement with a Novel 3D Printed Modular Prosthesis for Tumors." Therapeutics and Clinical Risk Management, vol. 14, Oct. 5, 2018, pp. 1897-1905., doi:10.2147/tcrm.s172442. (Year: 2018).*

(Continued)

*Primary Examiner* — Yashita Sharma
*Assistant Examiner* — Amanda M Barkan
(74) *Attorney, Agent, or Firm* — Heslin Rothenberg Farley & Mesiti PC; Kristian E. Ziegler, Esq.

(57) ABSTRACT

At least one embodiment comprises a talus implant comprising: a body section; a neck section; a crown, wherein the crown is positioned at a top portion of the body section; at least one wing coupled to the body section, wherein the wing extends out from the body section. At least one embodiment further comprises at least one screw hole positioned in at least one of the neck section and the body section. In at least one embodiment the outer surface of the implant is polished. In at least one embodiment a portion of the outer surface is polished while a portion of the outer surface is roughened.

14 Claims, 20 Drawing Sheets

(51) Int. Cl.
  *B33Y 50/00* (2015.01)
  *B33Y 80/00* (2015.01)
  *B29C 64/386* (2017.01)
  *G16H 50/50* (2018.01)
  *G16H 50/30* (2018.01)
  *G16H 30/40* (2018.01)
  *A61F 2/30* (2006.01)
  *B29L 31/00* (2006.01)

(52) U.S. Cl.
  CPC ............... *B33Y 10/00* (2014.12); *B33Y 50/00* (2014.12); *B33Y 80/00* (2014.12); *G16H 30/40* (2018.01); *G16H 50/30* (2018.01); *G16H 50/50* (2018.01); *A61F 2002/30116* (2013.01); *A61F 2002/30322* (2013.01); *A61F 2002/30578* (2013.01); *A61F 2002/30878* (2013.01); *A61F 2002/30909* (2013.01); *A61F 2002/30952* (2013.01); *A61F 2002/30985* (2013.01); *A61F 2002/4207* (2013.01); *B29L 2031/7532* (2013.01)

(58) Field of Classification Search
  CPC .... A61F 2/40; A61F 2/30767; A61F 2/30907; A61F 2002/4207; A61F 2002/30985; A61F 2002/30321; A61F 2002/30322; A61F 2002/30011; A61F 2002/30578; A61F 2002/30878
  See application file for complete search history.

(56) References Cited

U.S. PATENT DOCUMENTS

| | | | |
|---|---|---|---|
| 10,912,652 B2 * | 2/2021 | Fonte | A61F 2/40 |
| 10,952,865 B2 * | 3/2021 | Leemrijse | A61F 2/30749 |
| 2012/0191210 A1 | 7/2012 | Ratron | |
| 2017/0360488 A1 * | 12/2017 | Kowalczyk | A61B 17/8095 |

OTHER PUBLICATIONS

Ruatti, Sébastien, et al. "Total talar prosthesis replacement after talar extrusion." The Journal of Foot and Ankle Surgery 56.4 (Jul. 2017): 905-909. (Year: 2017).*

* cited by examiner

TALUS IMPLANT

CROSS REFERENCE TO RELATED APPLICATIONS

This application is a non-provisional application and hereby claims priority from U.S. Provisional Application Ser. No. 62/908,438 filed on Sep. 30, 2019, the disclosure of which is hereby incorporated herein by reference in its entirety. In addition the disclosures of Ser. Nos. 16/268,074, 15/614,423, 15/585,441 and 15/665,097 are hereby incorporated by reference in its entirety.

BACKGROUND OF THE INVENTION

The talus bone forms part of the ankle joint and interacts with the tibia and the fibula. The talus is also in contact with the calcaneus which is positioned below the talus and the navicular which is positioned in front of the talus on a person's foot. When a talus bone becomes compromised through necrosis or through an injury, there is a need to have the talus bone replaced.

Thus, at least one embodiment comprises a talus implant that includes a neck section, a body section and a crown. The talus implant can be printed in a substantially customized manner to suit the needs of a patient. In the past, talus implants would have to be machined or created from castings. However, with the onset of three dimensional printing, customized talus implants can be created.

SUMMARY OF THE INVENTION

At least one embodiment comprises a talus implant comprising a body section; a neck section and a crown, wherein the crown is positioned at a top portion of the body section. There is at least one wing coupled to the body section, wherein the at least one wing extends out from the body section.

At least one embodiment further comprises at least one screw hole positioned in at least one of the neck section and the body section.

In at least one embodiment, the body section has a length and the neck section has a length, wherein a length of the body section is approximately equal to a length of the neck section.

In at least one embodiment, the screw hole is positioned in the neck section.

In at least one embodiment, the wing comprises at least one of a posterior process.

In at least one embodiment, there is a post extending out from a bottom portion of the body section.

In at least one embodiment, there is a body section has a bottom surface and wherein the bottom surface of the body section is formed from a mesh structure.

In at least one embodiment, there is a bottom surface of the body section and the post are formed from a mesh structure.

In at least one embodiment, the neck section comprises at least two screw holes.

In at least one embodiment, there are two screw holes from the neck section to the body section.

In at least one embodiment, the crown is configured to have at least two separate rounded surfaces.

In at least one embodiment, the crown has a substantially semi-circular cross-section.

In at least one embodiment, the neck section further comprises at least one screw hole.

In at least one embodiment, the talus implant is printed in a three-dimensional manner.

In at least one embodiment, the neck section comprises at least three screw holes with at least two screw holes extending into the body section.

In at least one embodiment, the at least one post is formed from a mesh structure.

In at least one embodiment, the body section has a bottom surface that is formed from a mesh structure.

In at least one embodiment, the mesh structure is formed from a honeycomb pattern.

In at least one embodiment, the mesh structure has a varying porosity.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1A:
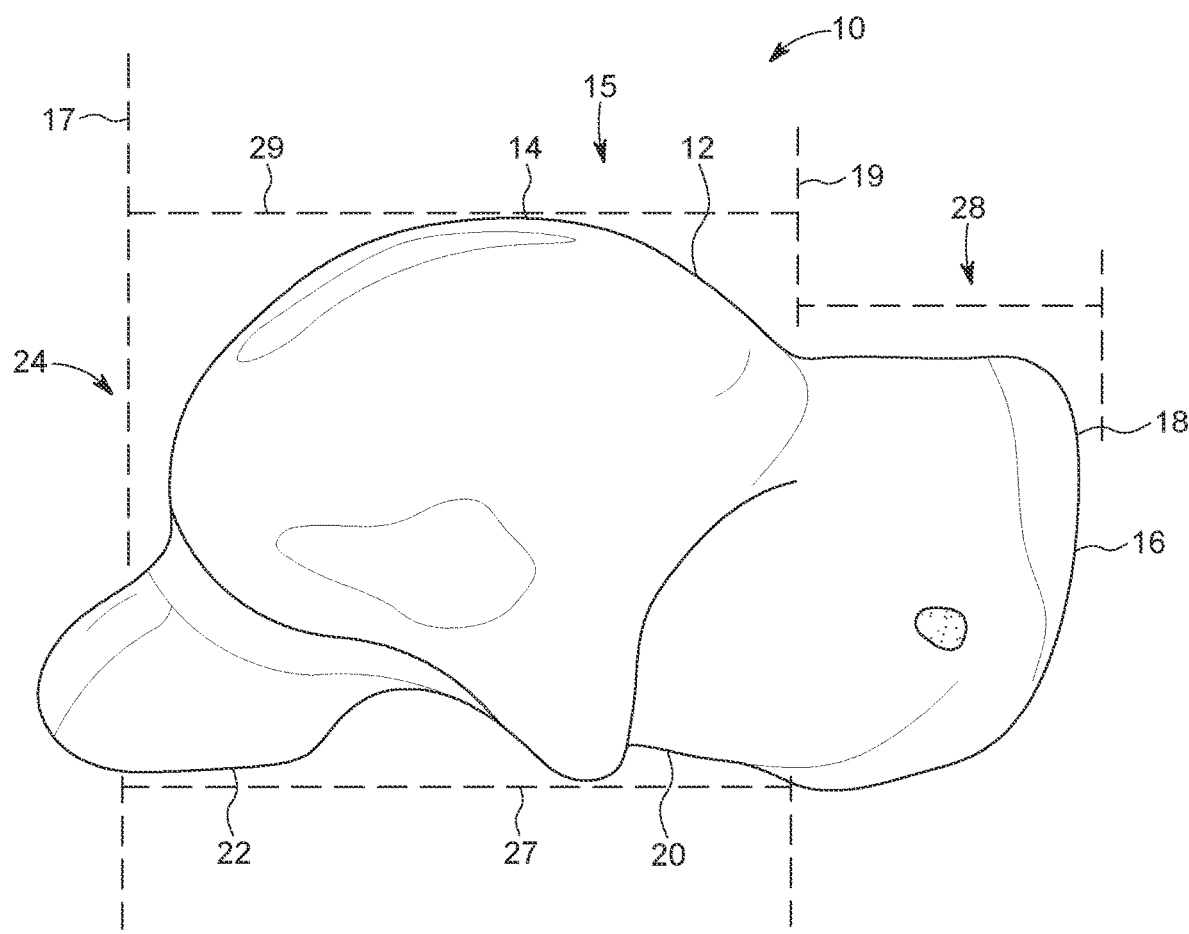
FIG. 1A is a side view of a first embodiment of a talus implant.

Referring to the drawings, FIG. 1A is a side view of a first embodiment 10 of a talus implant. With this embodiment 10 there is a body section 12 having a base body section 14, and a crown 15. The crown is formed as an articular surface for a tibia and is formed as a dome shape.

The body section 12 extends from a back of the talus implant to the beginning of the neck section. The body section 12 is bounded by dashed lines 17 and 19 and 27 and 29. The length of the body section is bounded by dashed lines 17 and 19. The height 24 of the body section is bounded by lines 27 and 29, wherein this height is approximately 36 mm such that the height in at least one embodiment is 37.7 mm and in another embodiment it is 35.7 mm.

A back end of the body section 12 shows wings 20 and 22. These wings are formed as flared out sections which are configured to rest over the calcaneus 54 (See FIG. 1D). Wings 20 and 22 form the lateral process (wing 20) and the posterior process (wing 22) respectively.

The neck section 16 includes a top surface 18 essentially forming a neck, wherein the neck extends out from the body 12 along a length 28 to the head 16. The head is configured for interaction with an adjacent navicular when the talar implant is implanted into an ankle joint.

Figure 1B:
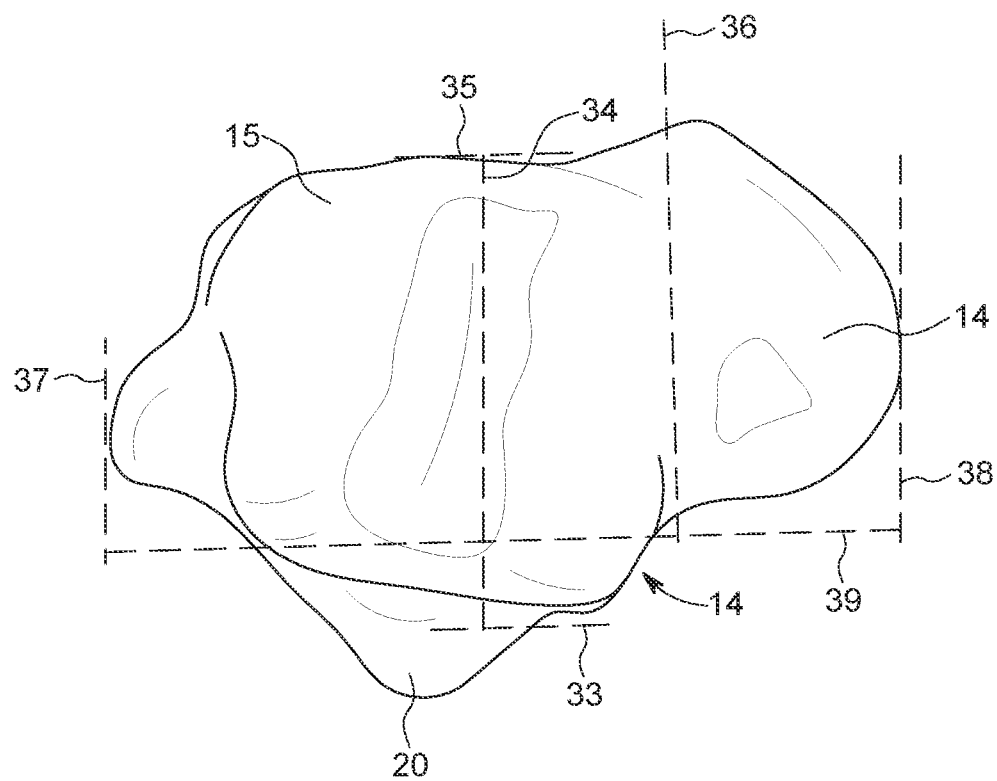
FIG. 1B is a top view of the embodiment of FIG. 1A.

FIG. 1B is a top view of the embodiment of FIG. 1A. With this design, there is shown a width 34 which is bounded by dashed lines 33 and 35 and which extends across crown or dome 15. In at least one embodiment the width is approximately 40 mm such as 42.4 mm in one embodiment and 40.4 in another embodiment. In addition, there is shown a length 39 which is bounded by dashed lines 37 and 38. In at least one embodiment the length can be approximately 65 mm (64.2 mm in one embodiment and 62.2 mm in another embodiment). The length of the neck is bounded by the dashed lines 36 to 38. In at least one embodiment the length of the neck is ⅓ of the entire length of the implant. In another embodiment the length of the neck is approximately ½ the entire length of the implant. In addition, the wing or lateral process 20 is shown extending out from body 14.

Figure 1C:
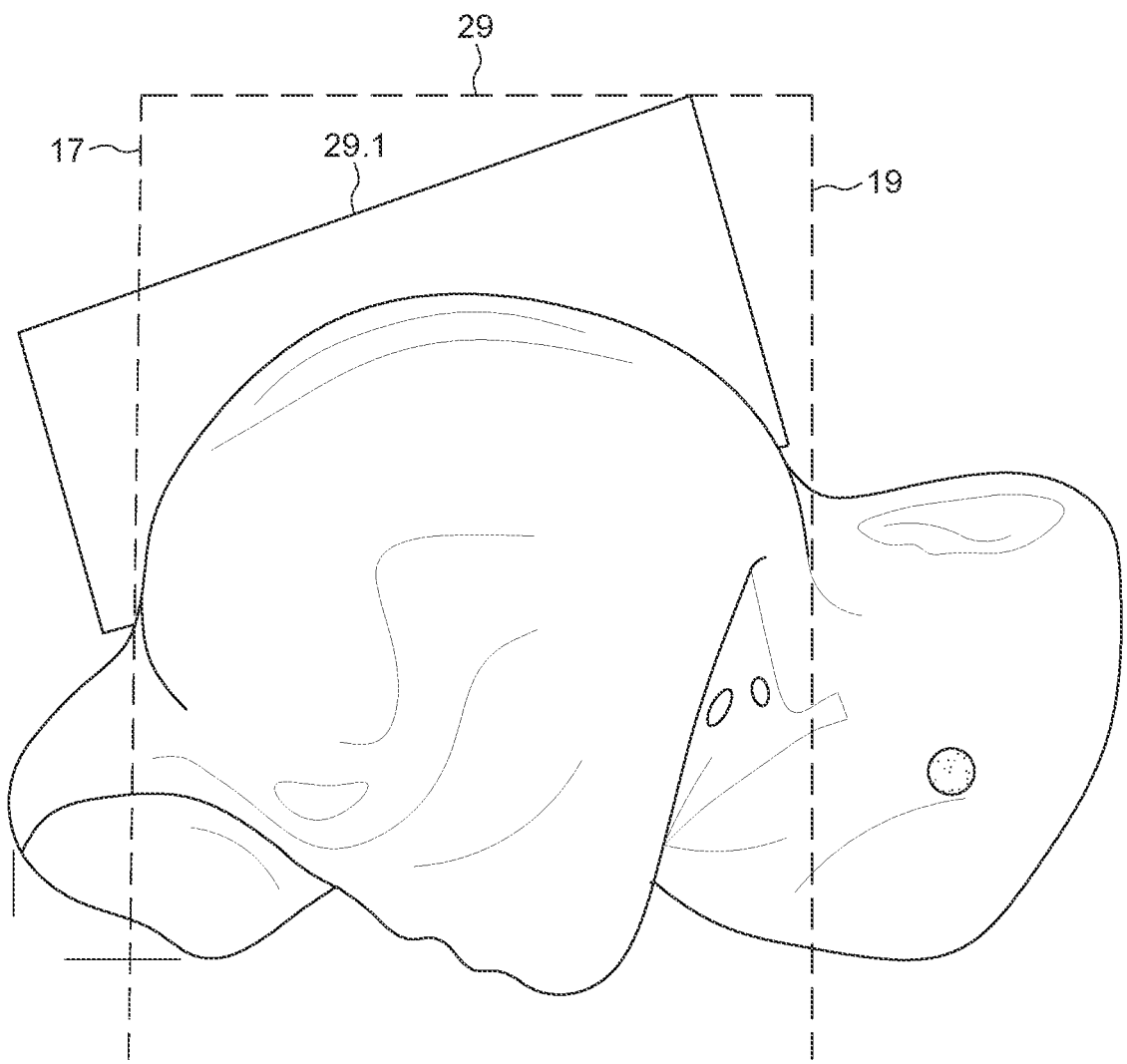
FIG. 1C is a side view of the talus implant with dimensions shown for the body.

FIG. 1C is a side view of the talus implant with dimensions shown for the body. With this view there is a dimension 29.1 which is for the body which is approximately 45 mm, wherein in at least one embodiment the length of the body section is 44.74 mm and in another embodiment the length is 43.20 mm. This length 29.1 is approximately the same length as length 29 as well.

Figure 1D:
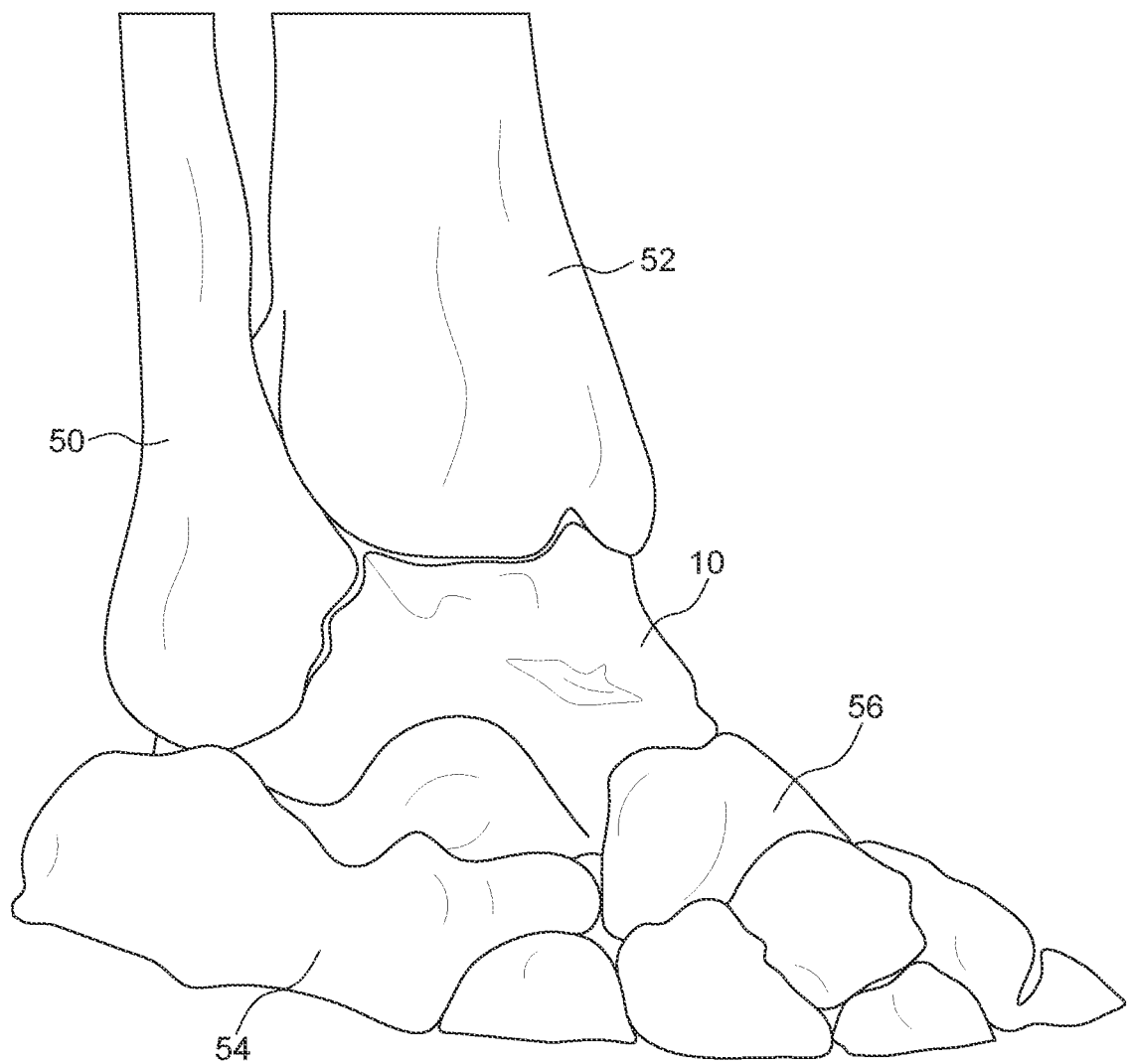
FIG. 1D is a perspective view of the embodiment of FIG. 1A inserted into an ankle joint.

FIG. 1D is a perspective view of the embodiment of FIG. 1A inserted into an ankle joint. With this design, the talus implant 10 is shown positioned below the fibula 50, the tibia 52, on top of the calcaneus 54 and adjacent to navicular 56. With the positioning of this talus implant 10 is configured to form a reconstructed ankle joint while allowing the user to still maintain all of the other bone parts in the joint. With the embodiment of the talus implant 10 all of the surfaces are polished such that the implant forms an entire bone such as a talus bone that has polished outer surfaces. These outer surfaces are configured to slide against the cartilage or soft tissue of the adjacent bone. The implant can be printed and then coated and then polished. For example, in at least one embodiment, the implant can be made from titanium in a 3D printed manner and then coated with a titanium nitride and then polished. In at least one embodiment the implant is printed using a cobalt chrome alloy which may or may not need polishing. In at least one embodiment the implant is polished, in another embodiment the implant is not polished.

Figure 2A:
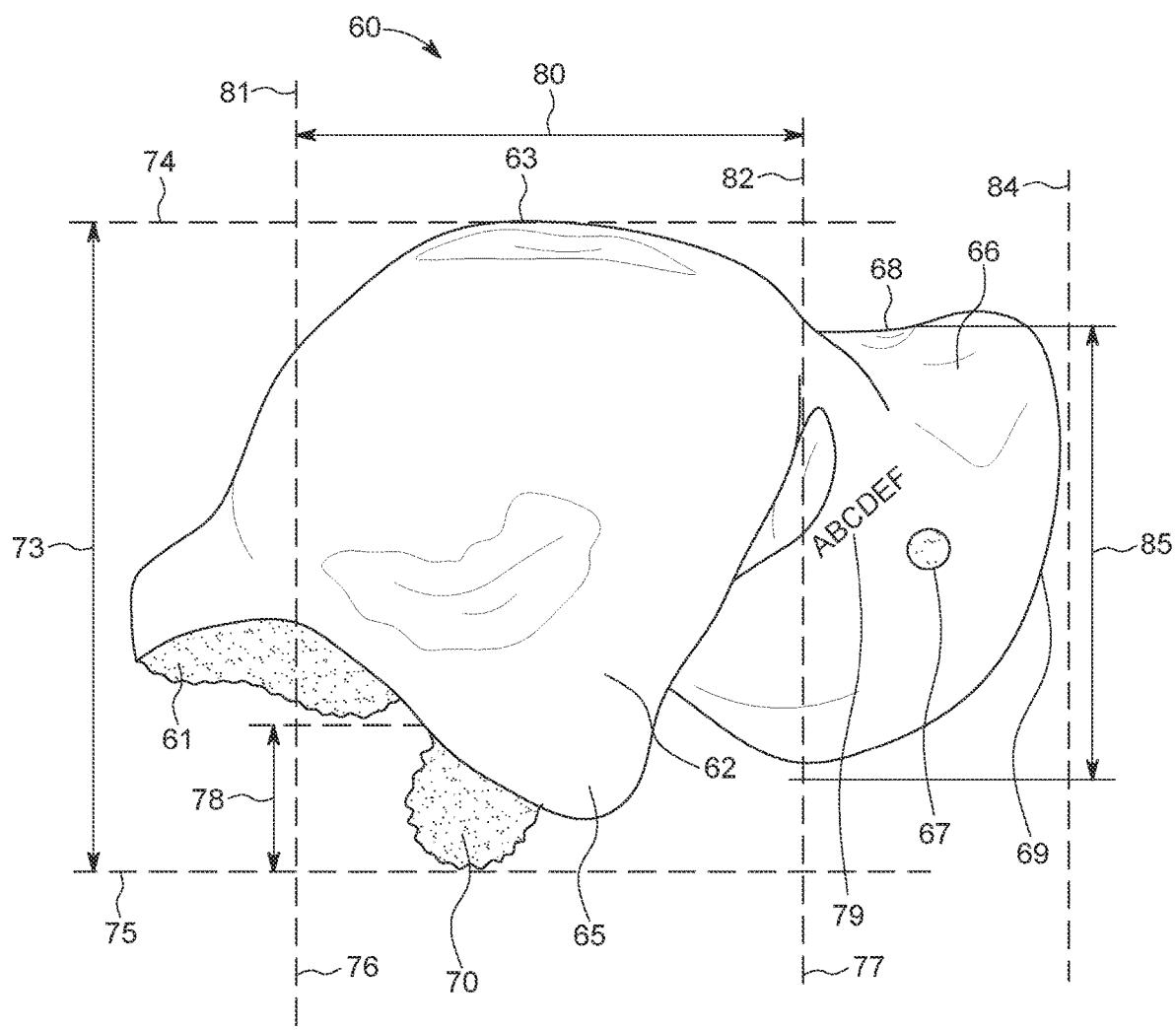
FIG. 2A is a side view of another embodiment.

FIG. 2A is a side view of another embodiment of an implant 60. With this embodiment, there is shown a body section 62, having a crown or dome 63. There is also a wing or posterior process 65. A neck 66 extends to a head 69. The neck has a top surface 68. Positioned in the neck 66 is a hole 67. There is a post 70 extending out from a bottom surface 61 of body section 62. The bottom surface 61 and post 70 is formed from a mesh which can have any suitable shape but in at least one embodiment is formed from a hexagonal shape having a varying porosity. The varying porosity of the mesh can be formed in different layers of differing porosity. Examples of varying porosity are found in Ser. No. 15/614,423 the disclosure of which is hereby incorporated herein by reference in its entirety. For example, a first outer layer of the mesh has a first porosity and a next inner layer of the mesh has a different porosity. In at least one embodiment, the outer layer of the mesh has a greater porosity than the inner layer of mesh. In another embodiment, the outer layer of the mesh has a lower porosity than the inner layer of the mesh. This talus implant can have a height 73 which extends from the post 70 to the top of the dome or crown 63 which is from dashed line 75 to dashed line 74. This post 70 can have a separate height 78 as well. The mesh actually extends beyond the outer frame.

The width of the body section 80 extends from a first dashed line 81 to a second dashed line 82. The height of the neck is shown by reference numeral 85 while the width or length of the neck is bound by dashed lines 82 and 84. In addition, there is shown a patient lock code 79 that is imprinted on the neck of the implant. The patient lock code is shown for illustration purposes in this and in other figures.

Figure 2B:
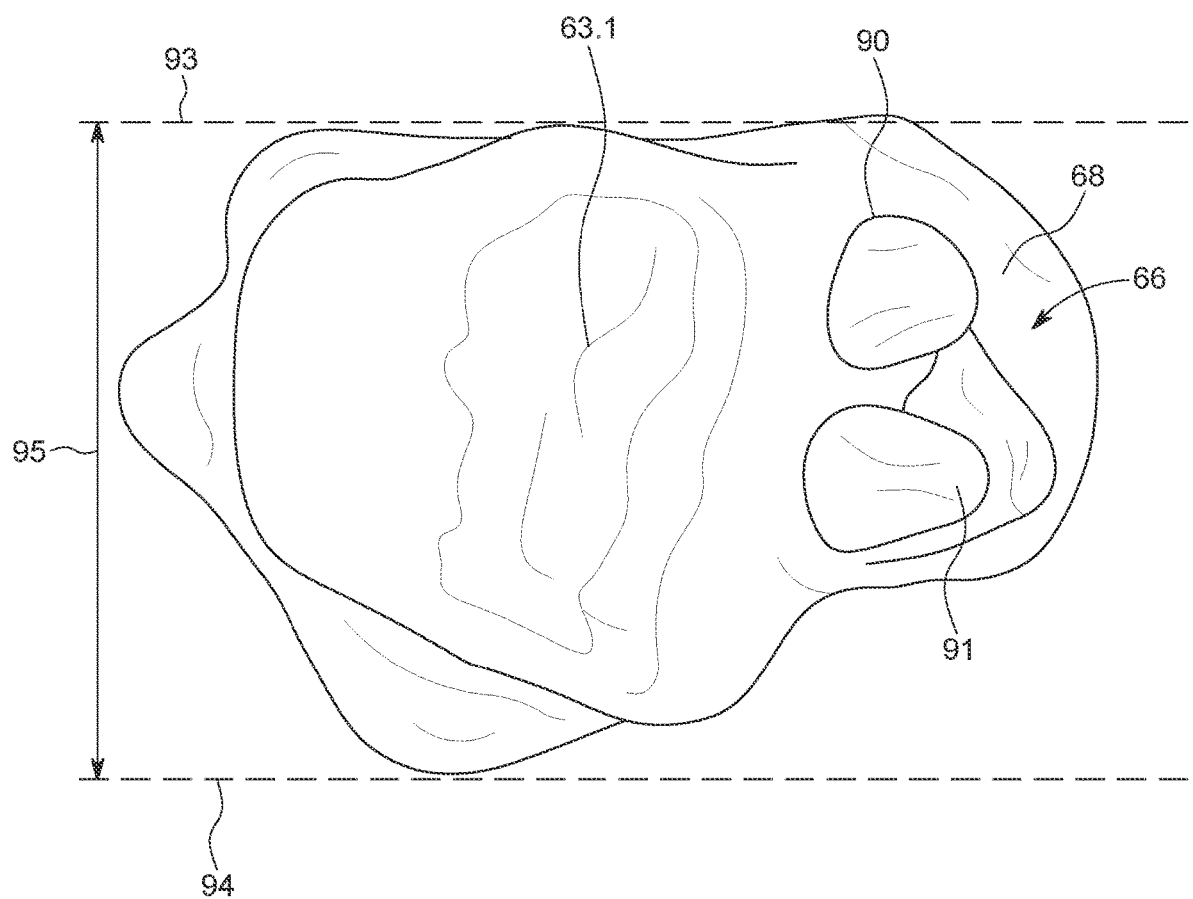
FIG. 2B is a top view of the embodiment of FIG. 2A.

FIG. 2B is a top view of the embodiment of FIG. 2A in this view there is a width 95 which is bound by dashed lines 93 and 94. This top view shows dome 63.1 as well as drill holes 90 and 91 which are drilled into top surface 68 of neck 66.

Figure 2C:
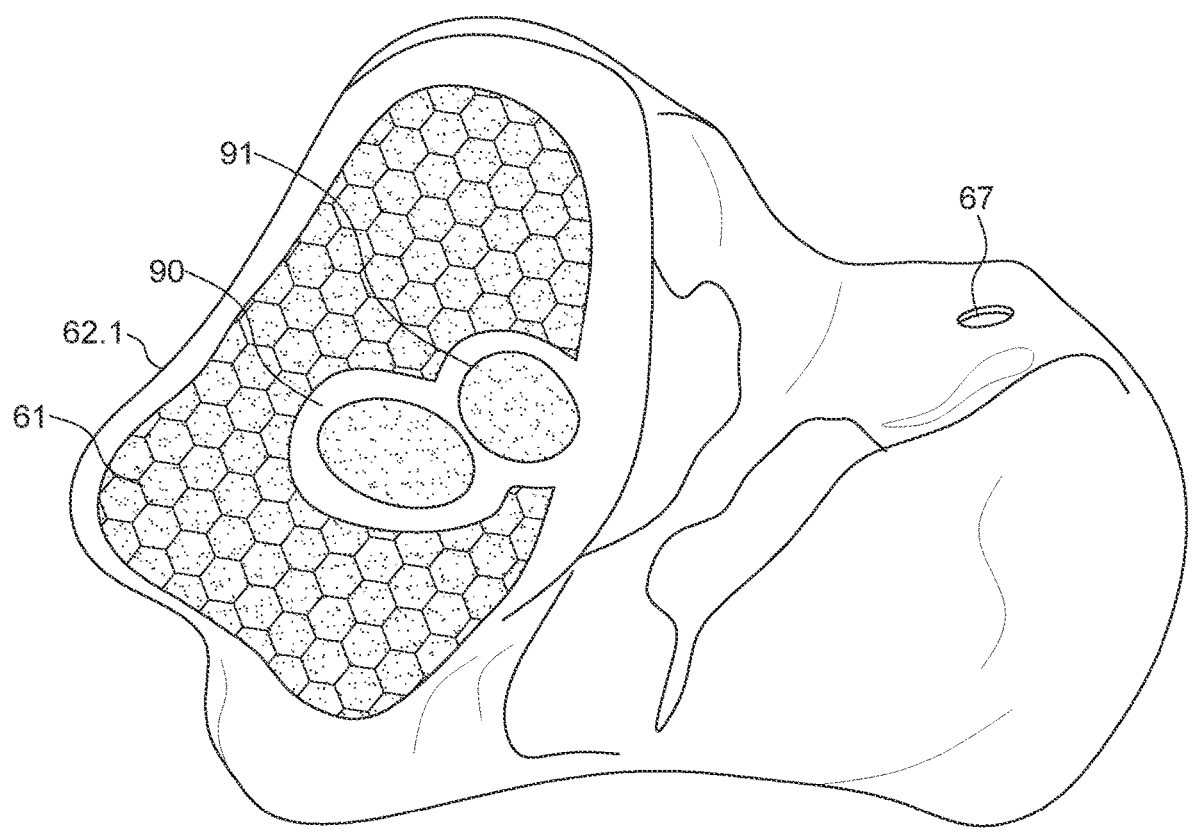
FIG. 2C is bottom view of the embodiment of FIG. 2A.

FIG. 2C is bottom view of the embodiment of FIG. 2A, in this view there is a bottom mesh surface 61 of body 62, wherein there are a plurality of drill holes 90 and 91 set therein. An additional hole 67 is also shown disposed in neck region 66, wherein this hole is configured to allow for holding of the implant when it is polished or coated after printing. In addition, mesh surface 61 is configured to extend beyond a frame 62.1 of body 62 such that this mesh extends below the bottom surface of the frame 62.1 and into an adjacent bone. That way the frame 62.1 does not form the first interactive connection with an adjacent bone. This extension of the mesh surface allows for greater bone growth into the mesh surface.

Figure 2D:
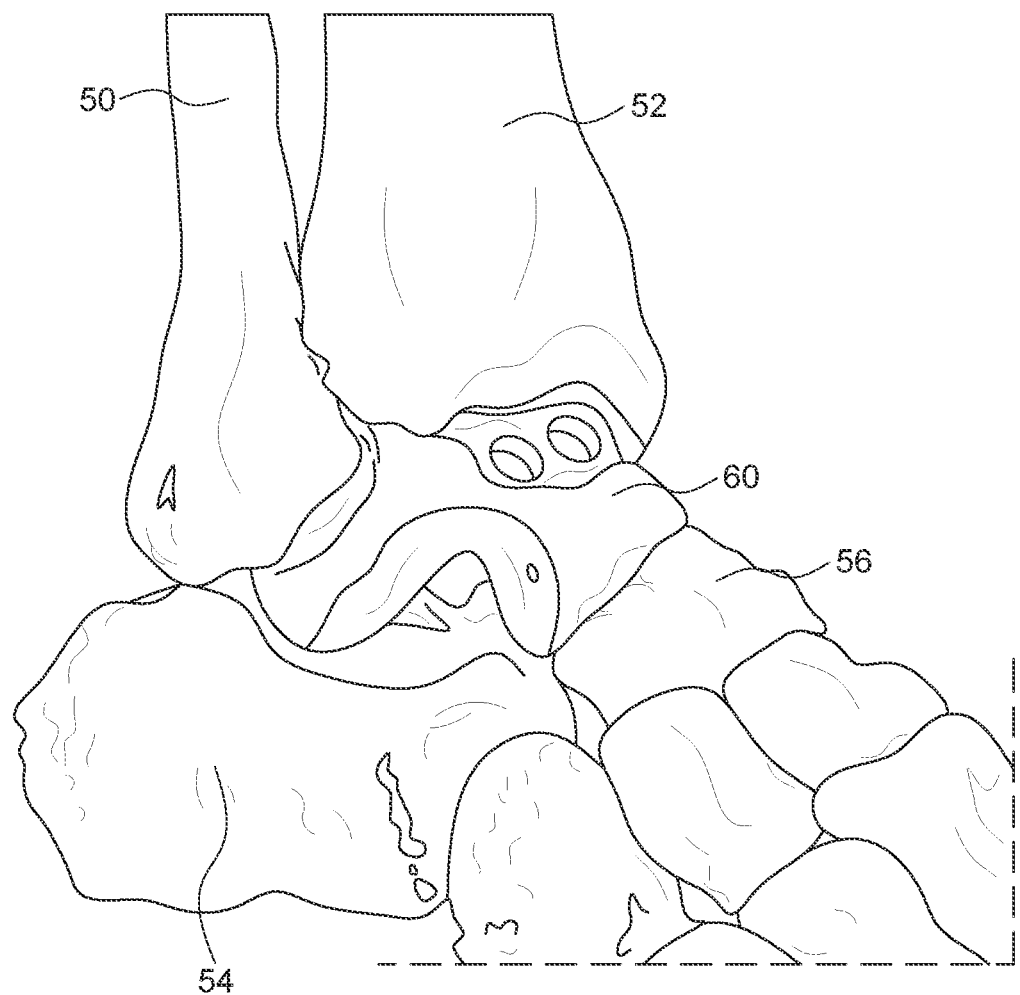
FIG. 2D is a perspective view of the embodiment of FIG. 2A inserted into an ankle joint.

FIG. 2D is a perspective view of the embodiment of FIG. 2A showing implant 60 inserted into an ankle joint. Thus, there is shown a fibula 50, a tibia 52, a calcaneus 54 as well as a navicular 56.

This embodiment of the implant 60 includes both a polished surface such as across the top side of the body and the neck as well as the head. There is a roughened surface formed along the bottom surface of the body section, wherein this bottom surface includes the post 70. The post 70 includes a solid core surrounded by a mesh. The mesh surface formed along the bottom surface 61 is a roughened surface having a mesh that can be formed with varying porosity. The geometry of this mesh is configured to have a lattice that in at least one embodiment is a honeycomb lattice with at least one interface having a hexagonal geometry. The surface of the lattice structure or mesh sits above or out and away from the frame so as to encourage interactions with other bone. The purpose of the mesh structure is to encourage bone growth into the mesh lattice structure. In each of the embodiments shown in FIGS. 2A-4D, that include a mesh or lattice structure the lattice in at least one embodiment includes a multi-layer lattice that has varying levels of porosity. In at least one embodiment the porosity of an outer layer of the mesh or lattice structure is lower i.e. more dense than an inner layer. In another embodiment, the porosity of the outer layer is higher, than an inner layer i.e. less dense on the outside than on the inside.

Figure 3A:
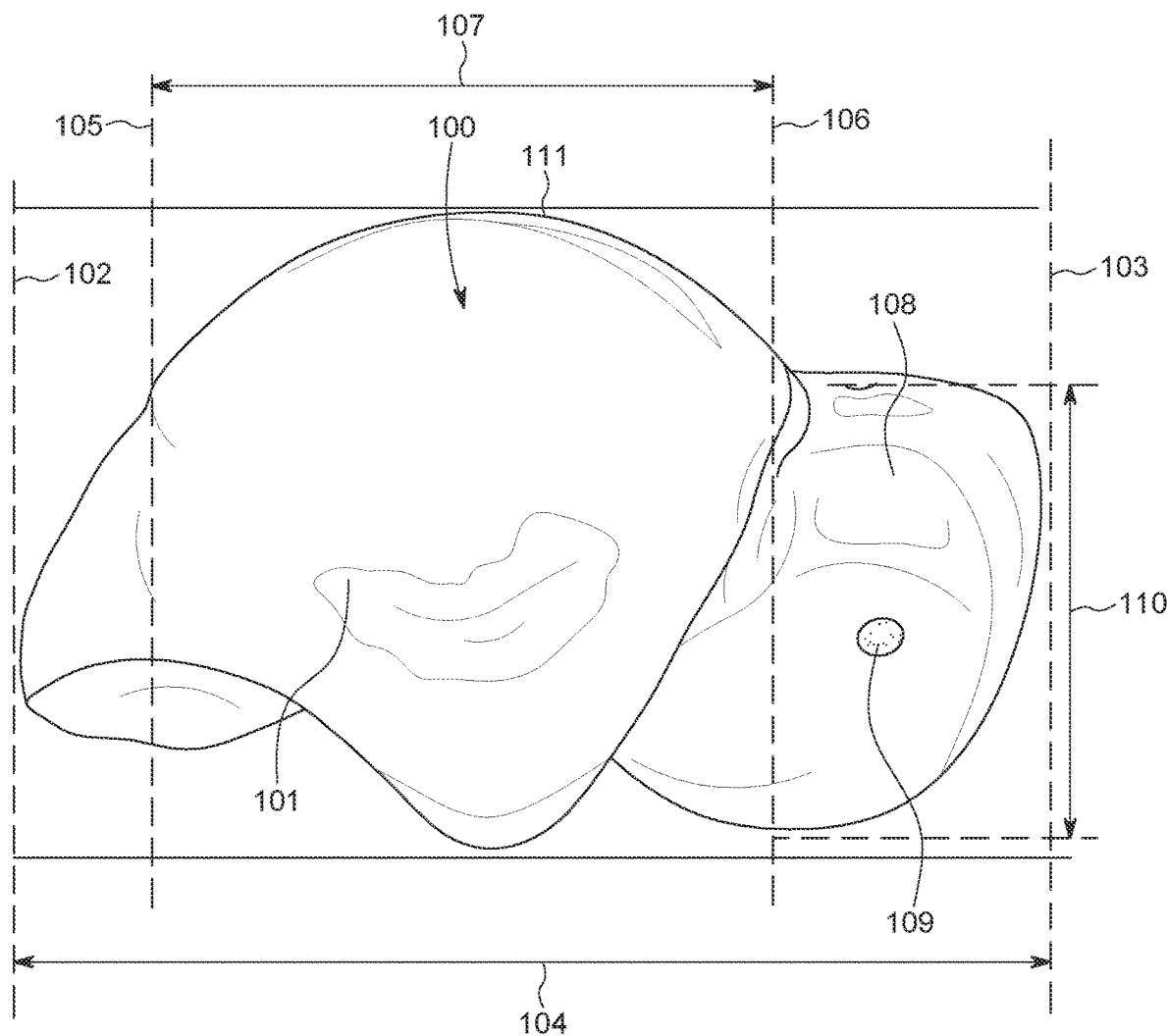
FIG. 3A is a side view of another embodiment.

FIG. 3A is a side view of another embodiment 100. With this embodiment there is a body section 101 as well as a dome or crown section 111. The length of the body section is bound by dashed lines 105 and 106 and the length is shown by arrow 107. The length of the entire implant is bound by dashed lines 102 and 103 and is shown by arrow 104. The height of the neck is shown by arrow 110. The neck 108 also includes a hole 109 as well. The length of the neck 108 is bound by dashed lines 103 and 106. As indicated above the length of the neck is approximately ⅓ of the overall length of the implant.

Figure 3B:
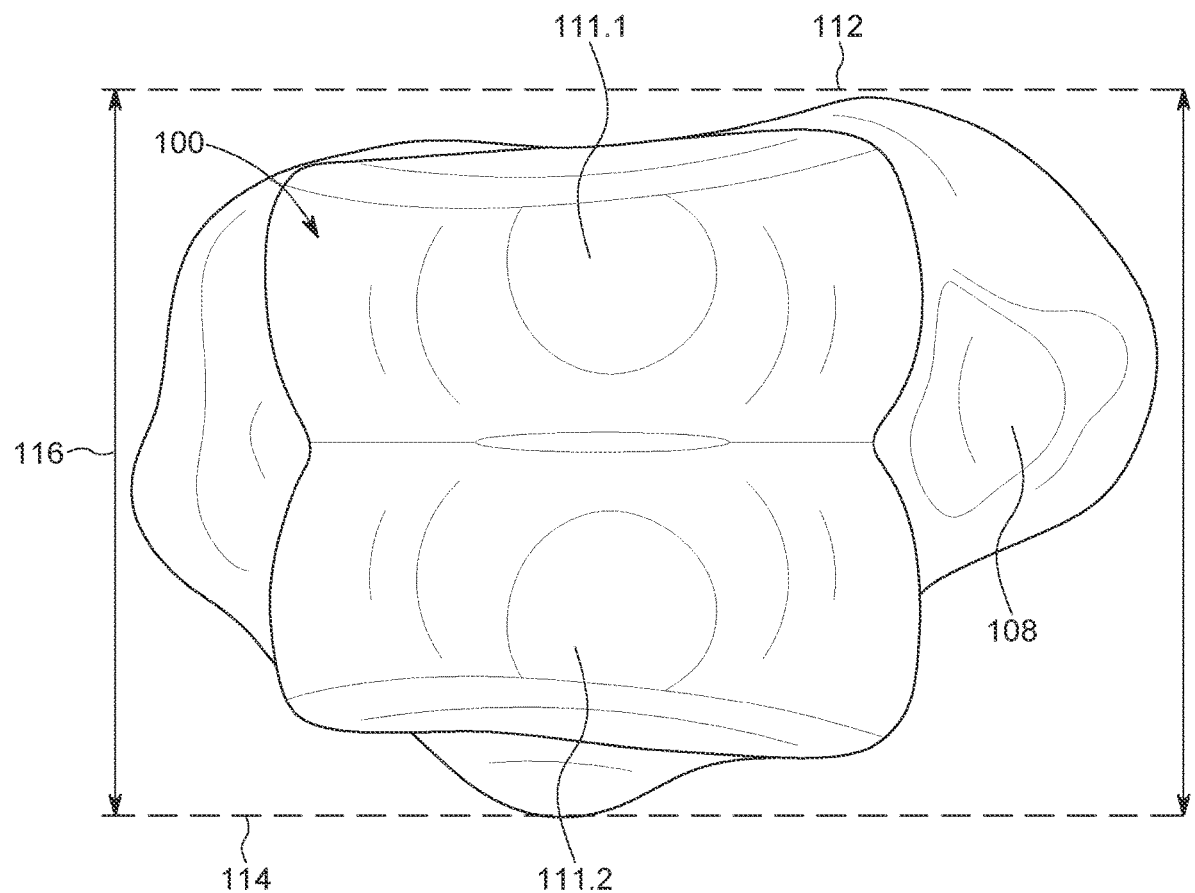
FIG. 3B is a top view of the embodiment of FIG. 3A.

FIG. 3B is a top view of the embodiment of FIG. 3A, wherein with this view, there is shown embodiment 100 which has a dome which has two crests such as crest 111.1 and crest 111.2. The width of this implant is bound by dashed lines 112 and 114 and wherein the width is shown by arrow 116.

Figure 3C:
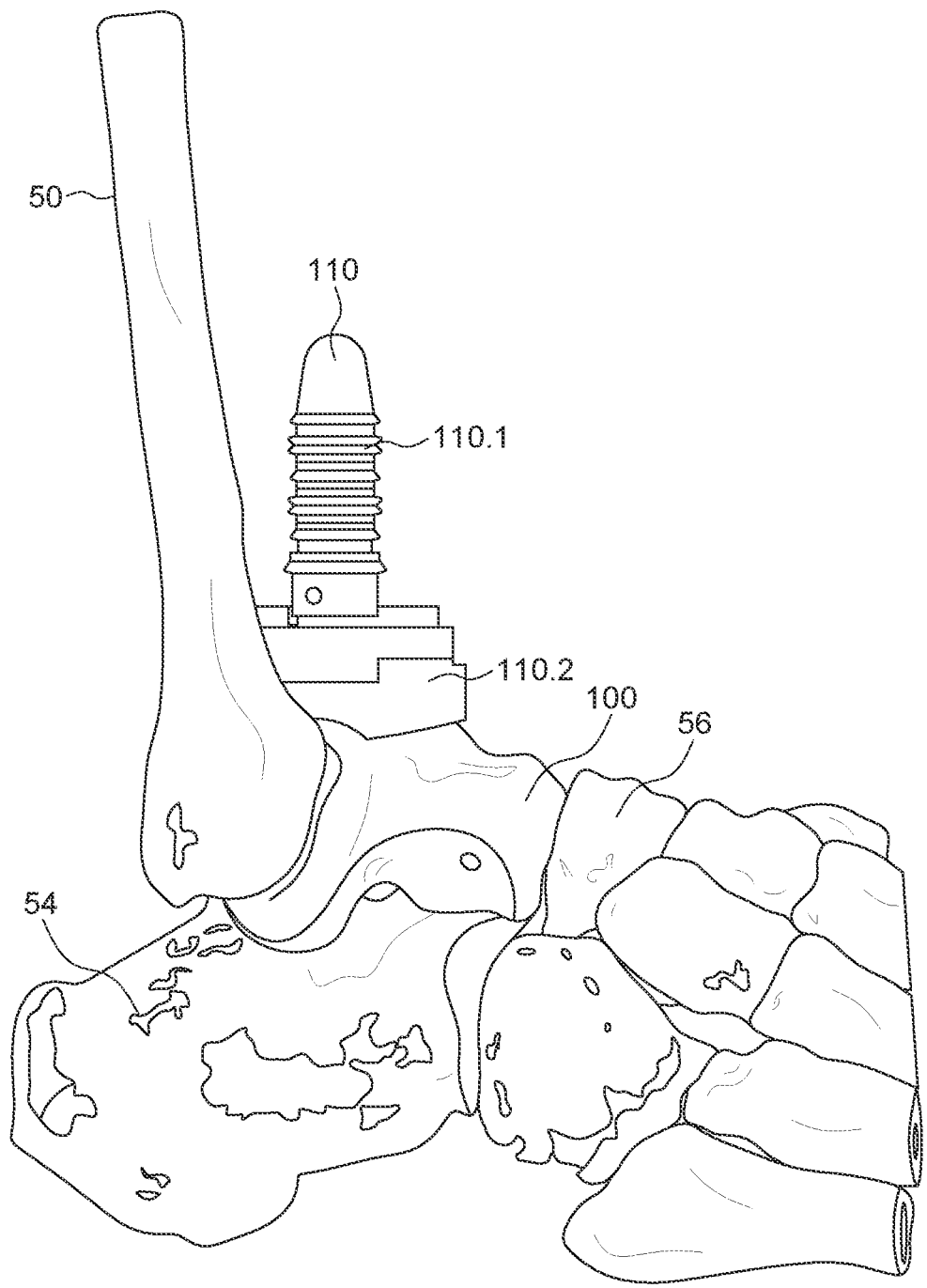
FIG. 3C is a side view of the embodiment of FIG. 3A inserted into an ankle joint.

FIG. 3C is a side view of the embodiment 100 of FIG. 3A inserted into an ankle joint. Thus, surrounding this implant embodiment 100 is a fibula 50, a calcaneus 54 and a navicular 56. In addition, disposed on top of implant 100 is a tibia implant 110 which includes a post 110.1 and a base plate 110.2. Base plate 110.2 is configured to interact with implant 100 and particularly contact the implant at the dome of the implant. Base plate 110.2 is configured as a plastic or poly based interactive surface for interacting with an adjacent talus implant.

Figure 4A:
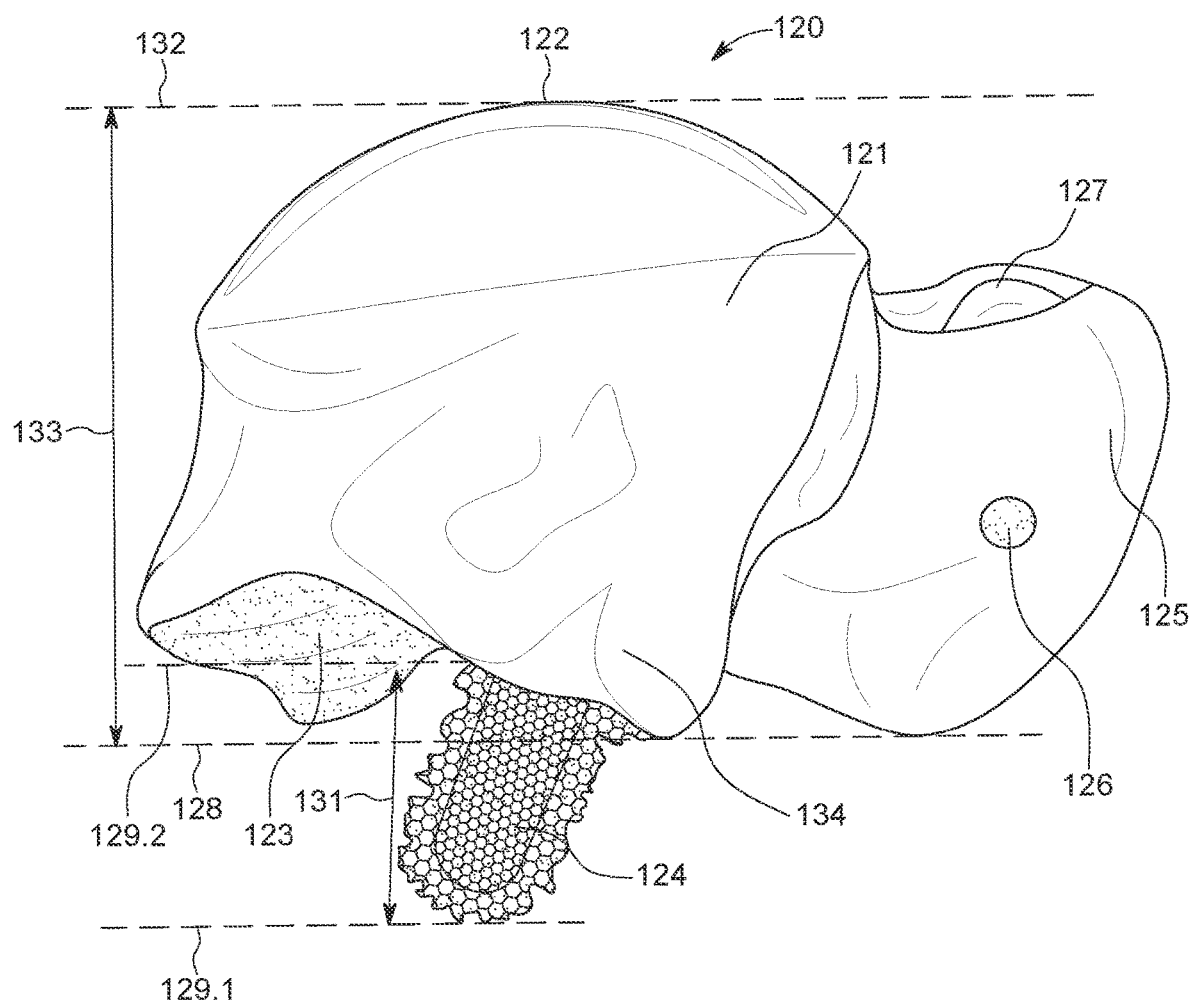
FIG. 4A is a side view of another embodiment.

FIG. 4A is a side view of another embodiment 120. With this embodiment, there is a base section 121, and a crown or dome portion 122. a neck 125 extends out to a head 150 (See FIG. 4C). An underside portion 123 of base section 121 is formed with a mesh. In addition, there is a post 124 which is also covered with a mesh. The mesh can be formed with a consistent porosity or with a porosity that varies and has different levels of porosity at different layers. The post 124 has a height 131 which is bounded by doted lines 129.1 and 129.2. The height of the talus implant is bound by dashed lines 128 and 132 and which is shown by arrow 133. Posterior process 134 is shown coupled to body section 121. Extending out from body 121 is neck 125. Neck 125 has hole 126 formed in the neck region for holding the implant when coating or polishing while drill hole 127 is formed in a top of the neck as well.

Figure 4B:
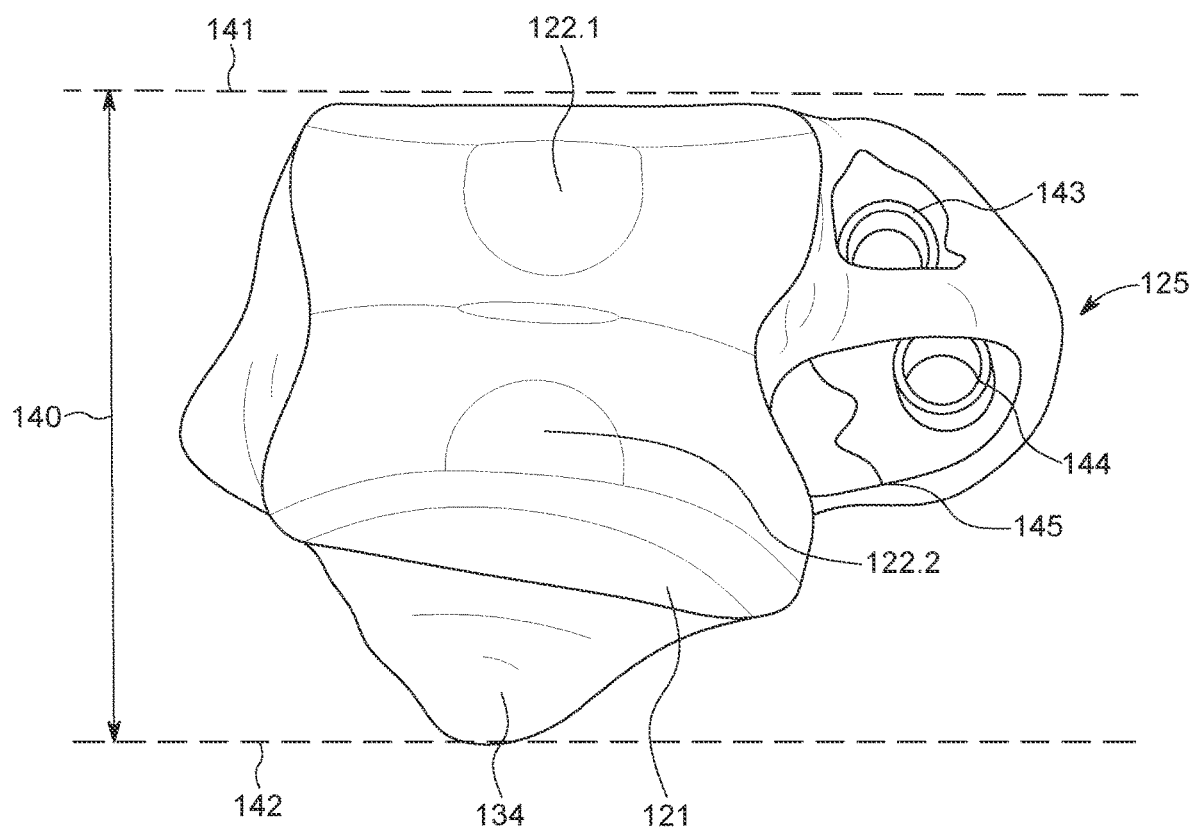
FIG. 4B is a top view of the embodiment of FIG. 4A.

FIG. 4B is a top view of the embodiment of FIG. 4A. The top view of this device shows dome or crown formed as two separate domes or crowns 122.1 and 122.2. The width of this implant 120 is shown as bound by dashed lines 141 and 142 and is shown by arrow 140. The posterior process 134 is shown extending out from the body 121. As shown, there are holes 143, 144 and 145 formed in neck region 125.

Figure 4C:
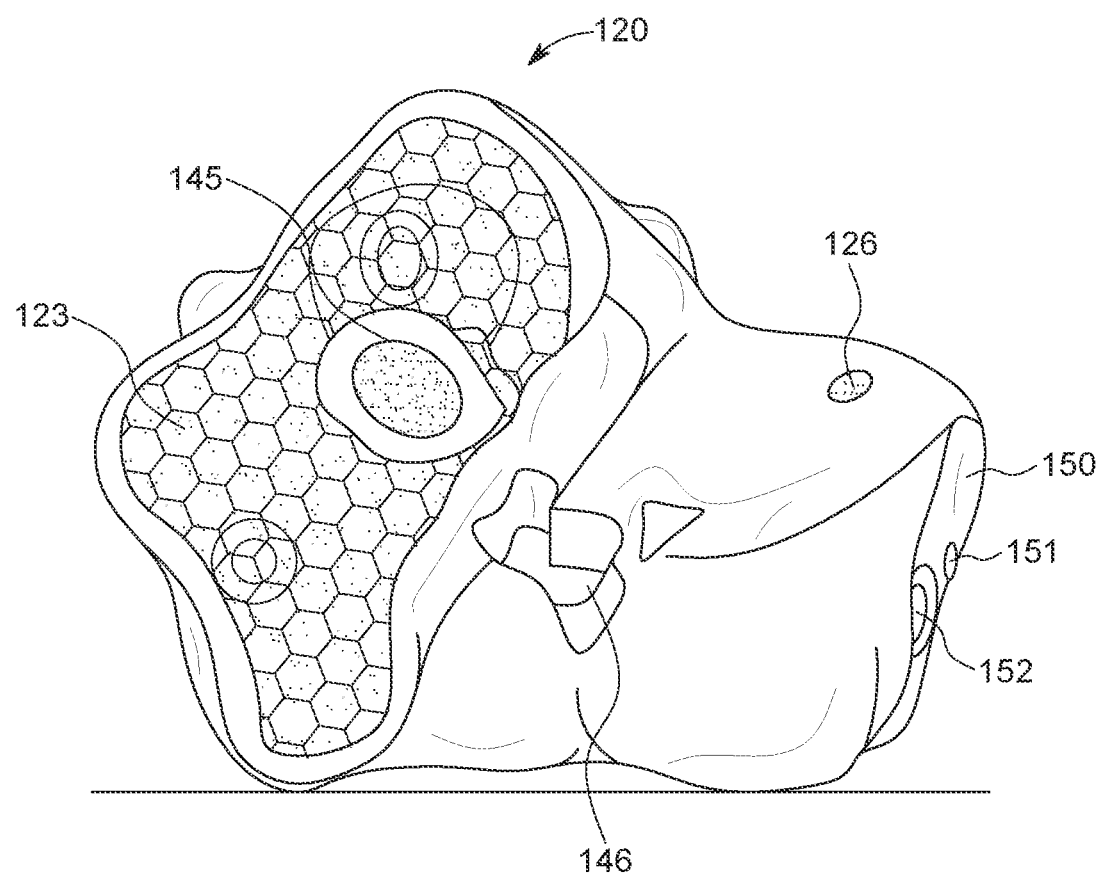
FIG. 4C is a bottom view of the embodiment of FIG. 4A.

FIG. 4C is a bottom view of the embodiment 120 of FIG. 4A. With this view there is shown bottom surface 123 having a drill hole 145. In addition, positioned in neck 125 is a drill hole 126 as well as drill hole 146 as well. In this view, head 150 is shown having drill holes 151 and 152. Head 150 includes a mesh surface for further interaction with an adjacent bone or bone structure.

Figure 4D:
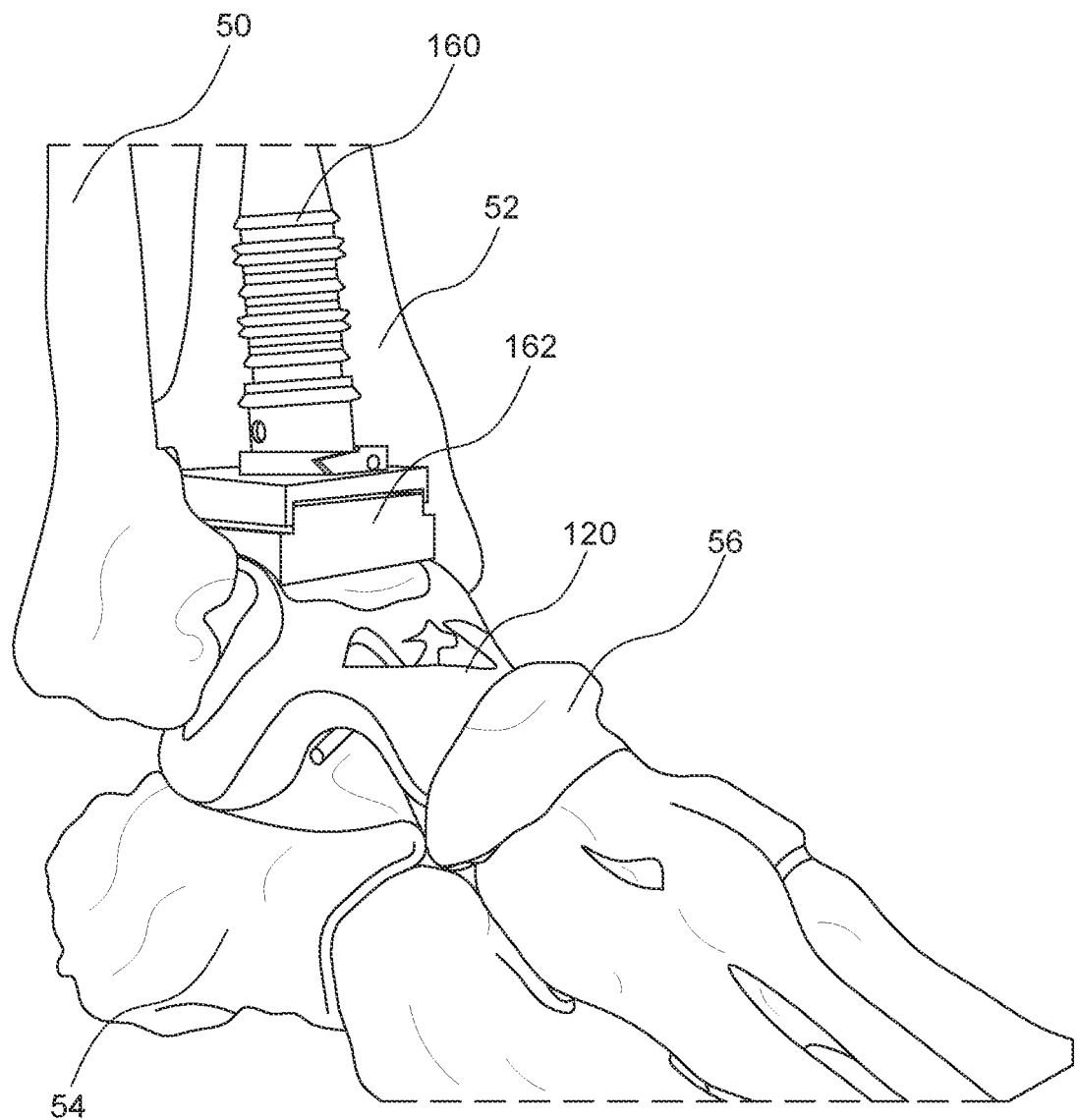
FIG. 4D is a perspective view of the embodiment of FIG. 4A inserted into an ankle joint.

FIG. 4D is a perspective view of the embodiment 120 of FIG. 4A inserted into an ankle joint. For example, there is shown implant 120 inserted adjacent to fibula 50. In addition, a tibia implant 160 having a base 162 is shown inserted into tibia 52. This tibia implant 160 has screw threads for engaging a compromised tibia bone. With the addition of plate 162, this plate is configured to interact with the dome or crown of the implant so that the domes or crowns 122.1 and 122.2 interact with plate to guide plate 161 along these domes or crowns. Plate 162 is configured as a plastic or poly type base for interaction with the adjacent talus implant. Disposed below the implant is a calcaneus bone 54 and disposed adjacent to the implant 120 is a navicular bone 56. The navicular bone 56 is configured to receive a head 150 having a mesh portion as well as screw holes 151 and 152. Therefore, screws can be inserted into these holes and then drilled into the adjacent navicular bone to secure the implant 120 to the adjacent navicular bone.

Figure 5A:
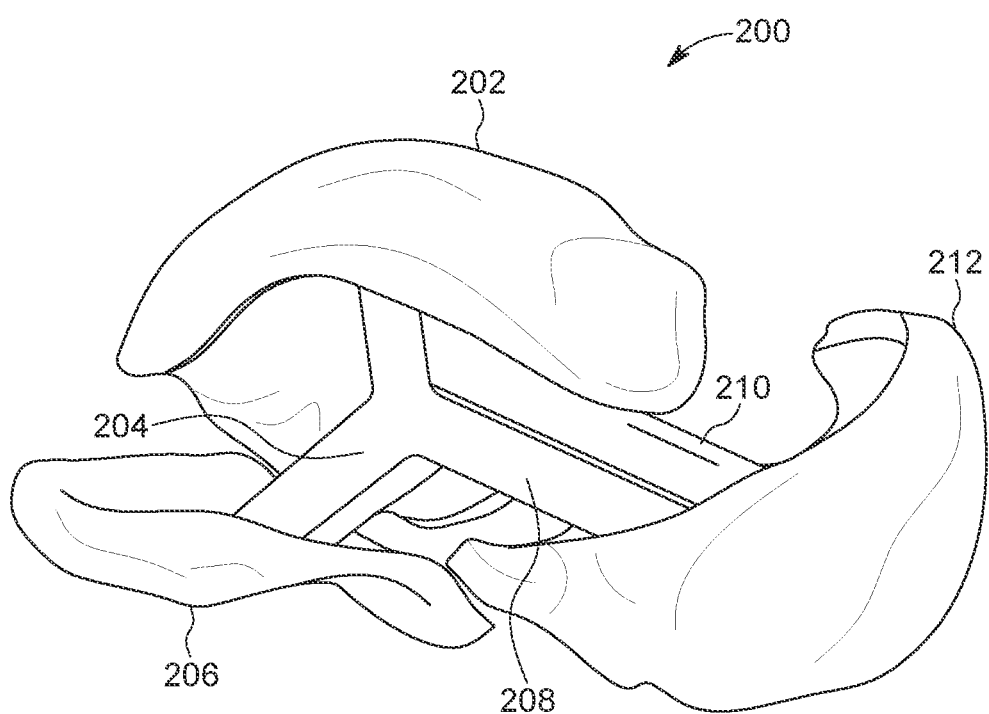
FIG. 5A is a side-perspective view of another embodiment which is a shell based embodiment.

FIG. 5A is another view of another embodiment of a shell talus implant design 200. With this design, there is a body section 202, as well as a head plate 212. There is also a bottom shield 206. The body section includes the crown or dome section described above. Coupled to body section 202 are a plurality of posts 204, 208 and 210. These posts space the different components including body section 202, head 212 and bottom shield 206 apart from each other wherein these posts suffice to replace the former solid block of an implant. Thus, the spacing of the head the bottom shield 206 and the body section 202 can result in a significant reduction in the amount of material necessary to make such an implant.

Figure 5B:
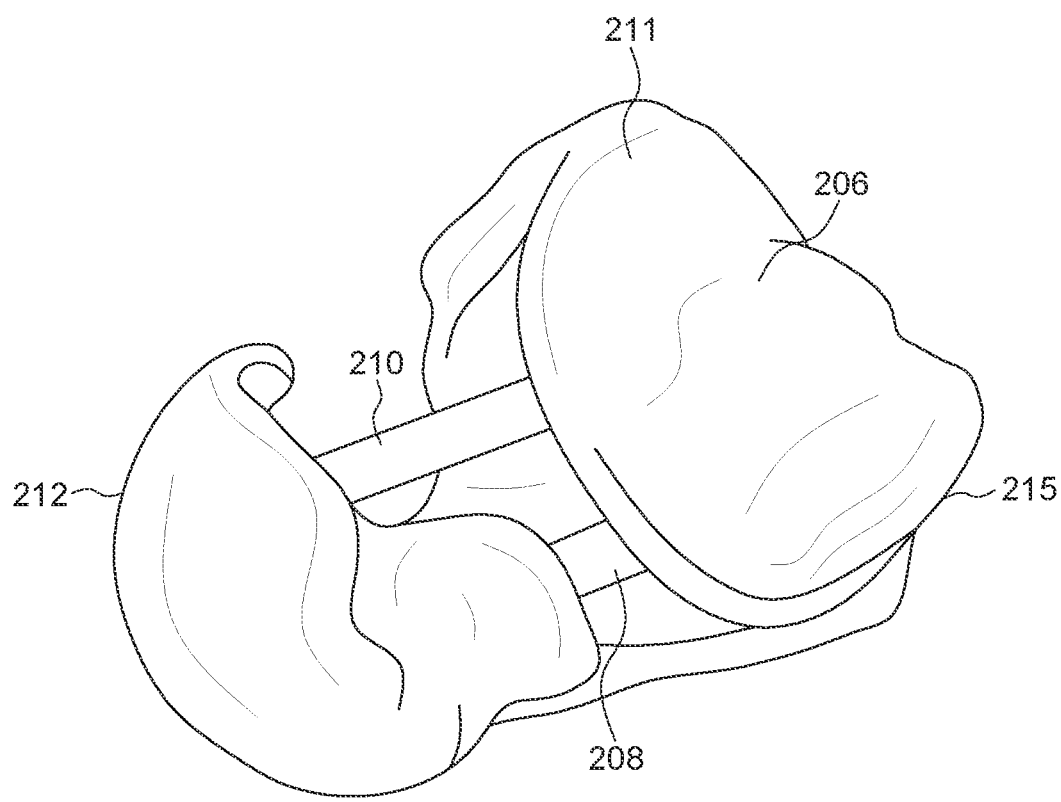
FIG. 5B is a bottom view of the embodiment shown in FIG. 5A.

FIG. 5B shows a bottom view of this design, wherein there is shown bottom shield 206 which is formed in a curved or substantially concave manner. This bottom shield 206 is configured to interact with the calcaneus. In addition, as shown in this view head 212 is configured spaced from the body section thereby creating a substantially open space between the body 202, the head section 212 and the bottom shield 206.

Figure 5C:
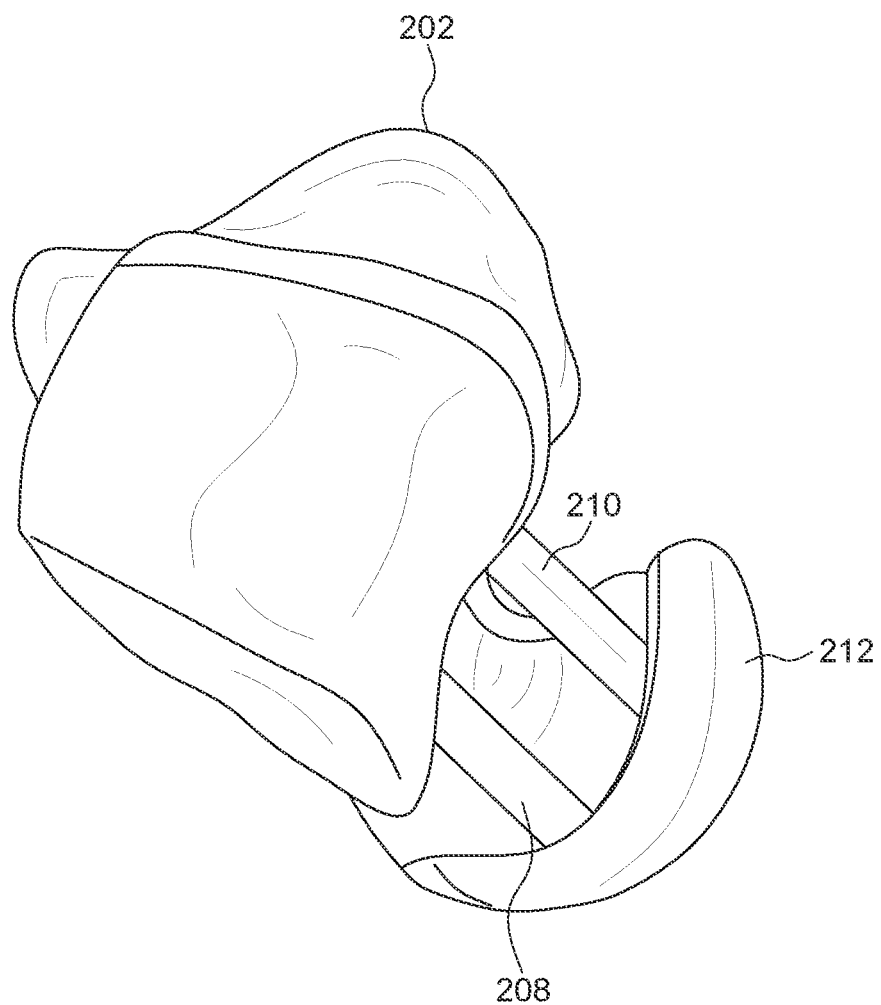
FIG. 5C is a top side perspective view of the embodiment shown in FIG. 5A.

FIG. 5C shows another view which shows the body section 202 which is separated from the head section 212 via posts 210 and 208.

Figure 5D:
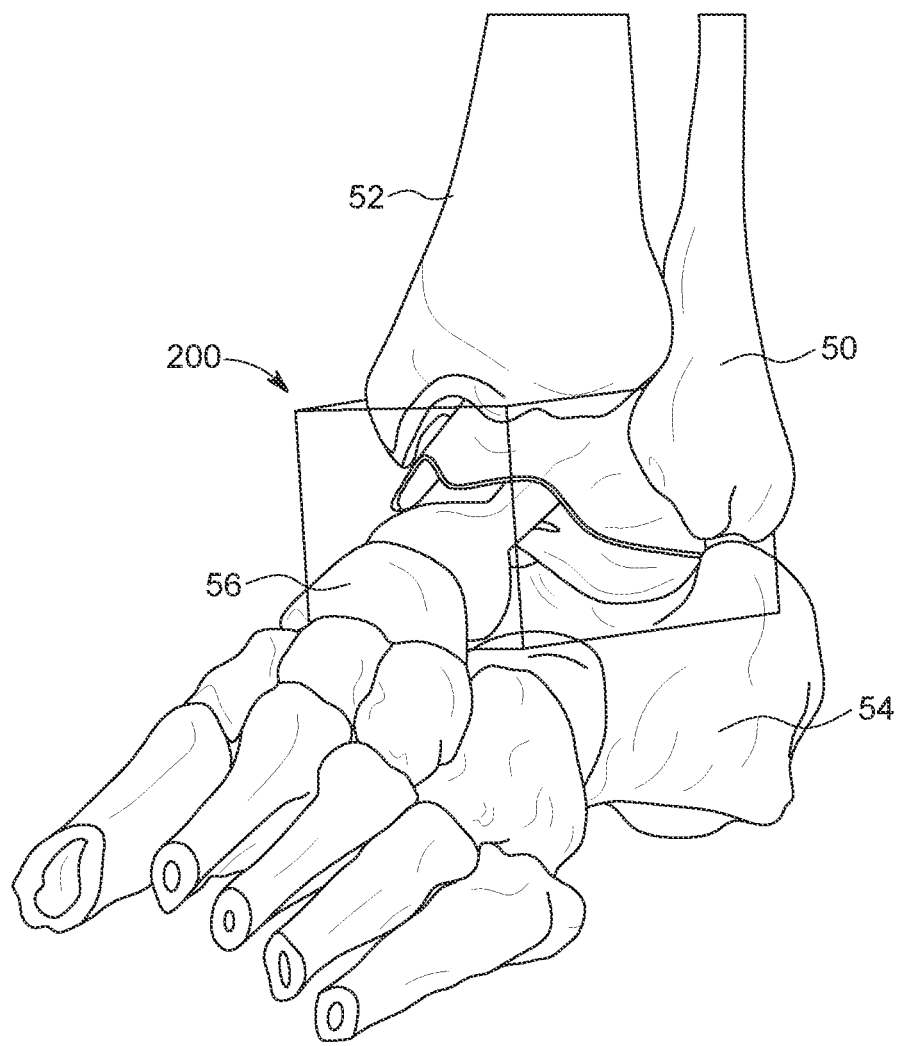
FIG. 5D is a view of the embodiment shown in FIG. 5A implanted into the ankle joint.
Figure 5E:
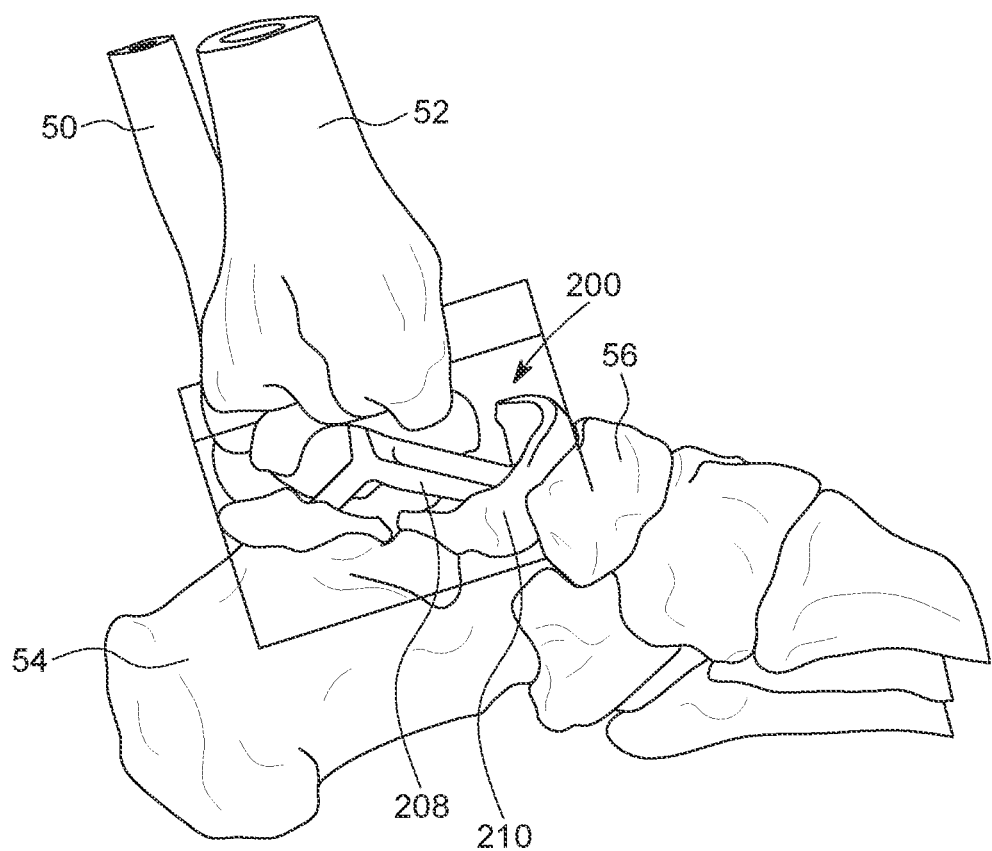
FIG. 5E is another view of the embodiment shown in FIG. 5A implanted into the ankle joint.

FIG. 5D shows a view of the implant 200 disposed into an ankle joint wherein there is shown adjacent to the implant in the implanted area, tibia 52, fibula 50, navicular 56, as well as calcaneus 54. As shown the posts 208 and 210 can be used to sufficiently space these components from each other to create a useful working ankle joint. FIG. 5E shows another view of this implant 200 inserted adjacent to tibia 52, fibula 50, calcaneus 54 as well as navicular 56. With these posts, 208 and 210, it allows for much less material to be used.

With these different designs, there is the possibility of repairing a plurality of different types of injuries to the ankle joint. For example, with the embodiments 60 and 120 there are shown posts which are configured to interact with an adjacent bone such as the calcaneus bone. In addition, with the case of the embodiments each of these different designs can be printed on demand to suit the injuries of the patients.

Accordingly, while at least one embodiment of the present invention have been shown and described, it is to be understood that many changes and modifications may be made thereunto without departing from the spirit and scope of the invention as defined in the appended claims.

What is claimed is:

1. A talus implant comprising:
   a body section;
   a neck section; and
   a crown positioned at a top portion of the body section,
   wherein at least one wing extends out from the body section,
   wherein the neck section comprises a plurality of coupling holes that extend into said body section, and
   wherein said body section, said neck section, said crown and said wing are made from a single piece of polished metal.

2. A talus implant comprising:
   a body section;

a neck section;

a crown positioned at a top portion of the body section;

at least one wing that extends out from the body section; and at least one post extending out from a bottom portion of said body section, wherein said neck section, said crown and said at least one wing have a top surface made from a single piece of polished metal, wherein said post is formed integral with said body section, and wherein the neck section comprises a plurality of coupling holes that extend into said body section.

3. The talus implant as in claim 2, wherein said body section has at least one polished surface, wherein said body section has a bottom surface, and wherein said bottom surface of said body section is formed from a mesh structure.

4. The talus implant as in claim 3, wherein a bottom surface of said body section and said post are formed from a mesh structure.

5. The talus implant as in claim 2, wherein said plurality of coupling holes extend from a top of said neck section to said body section and are configured to allow coupling members inserted into said coupling holes to contact two different bones positioned adjacent to said body section.

6. The talus implant as in claim 1, wherein said crown is configured to have at least two separate rounded surfaces.

7. The talus implant as in claim 6, wherein said crown has a substantially semi-circular cross-section.

8. The talus implant as in claim 1, wherein the talus implant is printed in a three-dimensional manner.

9. The talus implant as in claim 1, wherein the plurality of coupling holes of the neck section comprises at least three coupling holes with at least two coupling holes extending into said body section.

10. The talus implant as in claim 3, wherein said mesh structure is formed from a honeycomb pattern.

11. The talus implant as in claim 10, wherein said mesh structure has a varying porosity.

12. An implant system comprising:
    a talus implant comprising:
        a body section with at least one wing; and
        a neck section comprising a plurality of coupling holes that extend into said body section,
        wherein an outer surface on the body section is formed of a polished metal and configured to interact with cartilage of at least one bone; and
    a tibial implant comprising:
        a post configured to insert into a tibia of a patient; and
        a base plate, configured to interact with the body section of the talus implant.

13. The implant as in claim 12, wherein at least a portion of the body section has an outer surface that is roughened and formed from a mesh structure.

14. The implant as in claim 13, wherein the mesh structure extends outward from the body section such that the mesh structure is configured to interact with adjacent bone.

* * * * *